United States Patent [19]

Shimura

[11] Patent Number: 5,187,731
[45] Date of Patent: Feb. 16, 1993

[54] METHOD FOR QUANTITATIVELY ANALYZING BONE CALCIUM

[75] Inventor: Kazuo Shimura, Kanagawa, Japan

[73] Assignee: Fuji Photo Film Co., Ltd., Kanagawa, Japan

[21] Appl. No.: 858,634

[22] Filed: Mar. 27, 1992

[30] Foreign Application Priority Data

Mar. 28, 1991 [JP] Japan .................................. 3-064289

[51] Int. Cl.⁵ ............................................. G01N 23/04
[52] U.S. Cl. .................................. 378/207; 250/327.2
[58] Field of Search ................... 250/327.2 B, 327.2 C; 378/207

[56] References Cited

U.S. PATENT DOCUMENTS

| | | | |
|---|---|---|---|
| 4,855,598 | 8/1989 | Ohgoda et al. | 250/327.2 C |
| 5,049,746 | 9/1991 | Ito | 250/327.2 C |
| 5,122,664 | 6/1992 | Ito et al. | 250/327.2 C |

Primary Examiner—Constantine Hannaher
Assistant Examiner—Don Wong
Attorney, Agent, or Firm—Sughrue, Mion, Zinn, Macpeak & Seas

[57] ABSTRACT

Radiation images are recorded with several kinds of radiation having different energy distributions and having passed through an object and a bone calcium reference material composed of sections simulating amounts of bone calcium varying step-wise, the object being constituted of bones and soft tissues. A bone image, in which only the patterns of the bones are formed or emphasized, is formed from the radiation images. A difference between a mean value of image signal components, which represent part of the pattern of each section of the bone calcium reference material in the bone image, and a mean value of background signal components, which represent areas in the vicinity of the pattern of each section of the bone calcium reference material, is calculated. A difference between a mean value of image signal components, which represent a pattern of a specific part of the bones in the bone image, and a mean value of background signal components, which represent areas in the vicinity of the pattern of the specific part of the bones, is calculated. The difference value calculated for the specific part of the bones is compared with the difference values calculated for the sections of the bone calcium reference material.

4 Claims, 5 Drawing Sheets

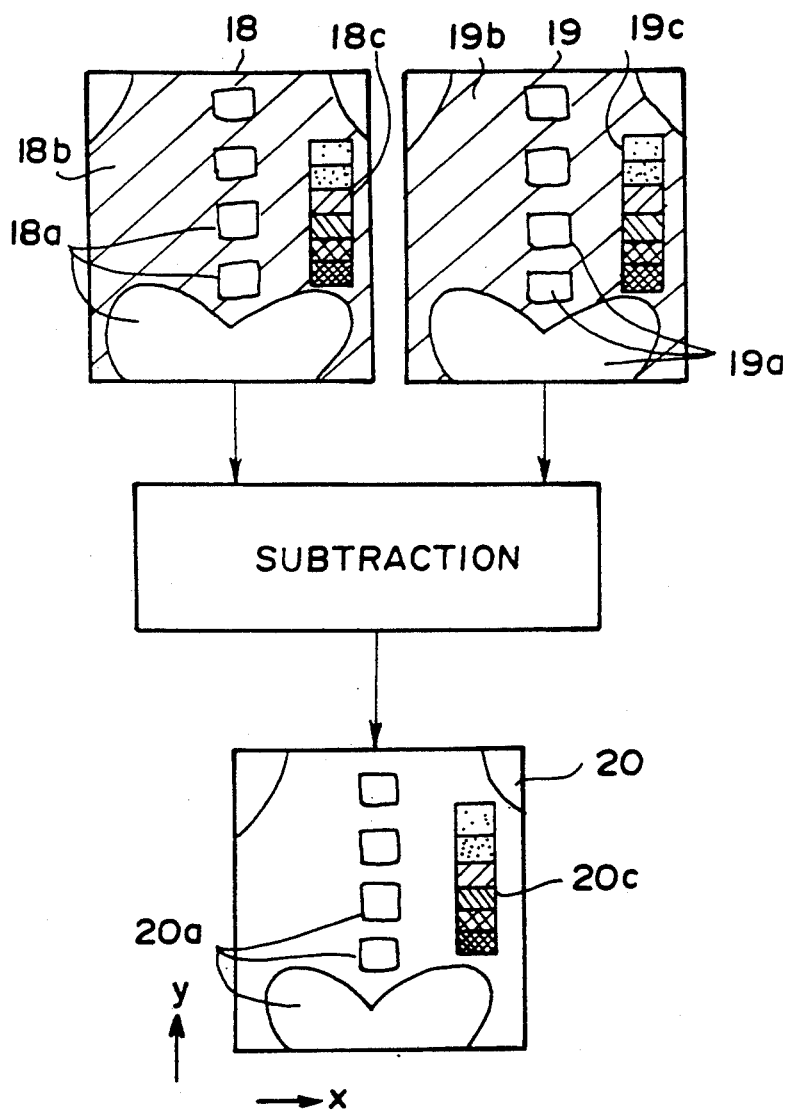

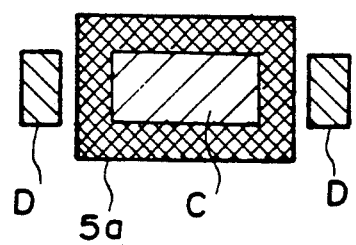
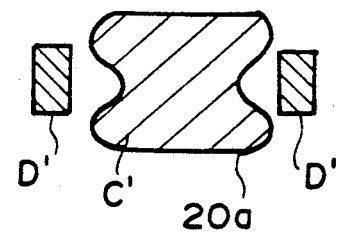
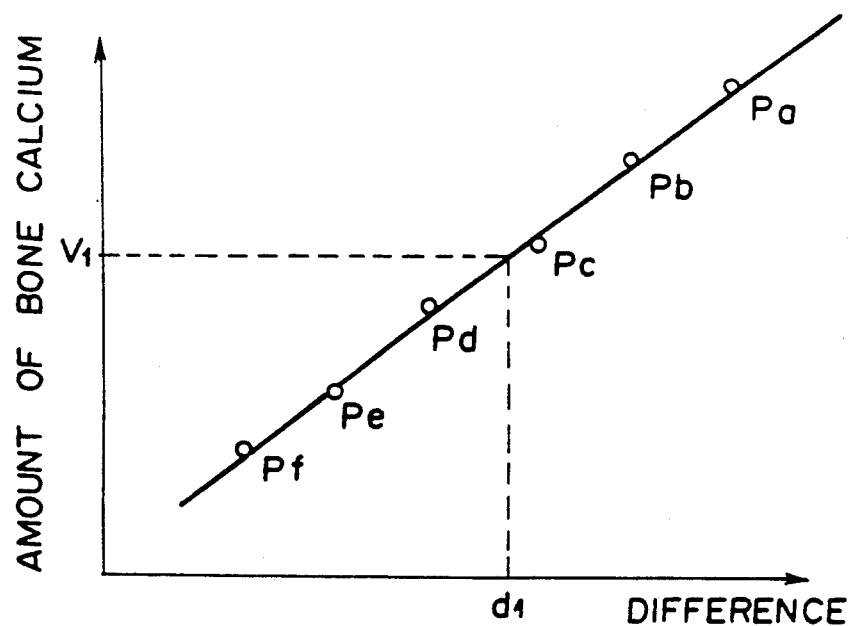

METHOD FOR QUANTITATIVELY ANALYZING BONE CALCIUM

BACKGROUND OF THE INVENTION

1. Field of the Invention

This invention relates to a method for quantitatively determining amounts of calcium in bones of a human body, or the like. This invention particularly relates to a method for quantitatively analyzing bone calcium, wherein an energy subtraction processing technique is utilized.

2. Description of the Prior Art

Quantitatively determining amounts of calcium in bones is necessary for preventing fractures of bones. Specifically, by investigating small changes in the amounts of calcium contained in bones, osteoporosis can be found early, and fractures of the bones can be prevented.

Therefore, various methods for quantitatively determining amounts of calcium in bones have been proposed and used in practice. Such methods are listed below.

i) Microdensitometry (MD Method)

With the MD method, a middle finger bone and an aluminum step wedge (a step-like pattern) are simultaneously exposed to X-rays, and an X-ray image is thereby recorded which is composed of a pattern of the middle finger bone and a pattern of the aluminum step wedge. The image density of the X-ray image is then determined by using a densitometer. Thereafter, the X-ray absorption amount of the middle finger bone is calculated with reference to the pattern of the aluminum step wedge and corrected in accordance with the width of the bone. In this manner, the amount of calcium in the bone is determined quantitatively. This method can be carried out with a simple apparatus. However, this method has the drawbacks in that the accuracy, with which the amounts of calcium in bones are determined quantitatively, cannot be kept high, and amounts of calcium in vertebral bones, which very well indicate the sign of an osteoporosis, cannot be determined.

ii) Single Photon Absorptiometry (SPA Method)

With the SPA method, γ-rays having a low energy level are irradiated to a bone, and the g-rays, which have passed through the bone, are detected by a scintillation detector spaced approximately 15 cm away from the bone. An analog calculation is made from a change in the count of the γ-ray quanta, and the weight of the bone per unit length is thereby calculated. With this method, amounts of calcium in bones can be determined more accurately than the MD method. However, this method has the drawbacks in that amounts of calcium in vertebral bones cannot be determined, a particular management must be done during the use of a radioisotope, and the source of the radiation must be exchanged frequently because of its half-life.

iii) Dual Photon Absorptiometry (DPA Method)

With the DPA method, a nuclide, G1153, which has two energy peaks of 44 keV and 100 keV, is employed as a radiation source. The amount of calcium in a bone is determined from a difference between the amounts of the two types of radiations having different energy levels, which have passed through a bone. This method is advantageous in that amounts of calcium in lumbar vertebrae and cervixes of thighbones can be determined, and the amount of calcium in bones of the whole body and the amount of fat of the whole body can be determined accurately. However, this method has the drawbacks accompanying the use of a radioisotope. Also, in order for radiation to be scanned, a long time is taken for the inspection to be carried out (for example, a time of more than ten minutes is required when the sample is a lumbar vertebra, and a time of 30 to 40 minutes is required when the sample is the whole body).

iv) Quantitative Digited Radiography (QDR Method or DPX Method)

The QDR method comprises nearly the same steps as those of the DPA method, except that, instead of a radioisotope being used, a pulsed X-ray source is combined with a filter in order to yield two types of radiation having different energy levels. With this method, good reproducibility can be obtained, and the inspection time can be kept comparatively short (approximately one third of the time required in the DPA method). This method is most advantageous from the point of view of simplicity and performance. However, the inspection time required is not very short (e.g. a time of as long as approximately six minutes is required when the sample is a lumbar vertebra), and should be kept shorter.

v) Quantitative Computer Tomography (QCT Method)

With the QCT method, an X-ray CT scanner is used, and the amount of calcium in, primarily, the third lumbar vertebra is determined on the basis of the CT number. In order to carry out this method, a large-scaled apparatus must be used.

vi) Dual Energy Quantitative Computer Tomography (DQCT Method)

The DQCT method is carried out in the same manner as that in the QCT method, except that two types of radiation having different energy levels are utilized and energy subtraction processing is carried out. This method is advantageous in that quantitative determination can be carried out which is free of adverse effects of fat contained in bone tissues. However, in order to carry out this method, a large-scaled apparatus must be used.

As described above, the conventional methods for quantitatively analyzing bone calcium, which are simple, have the problem in that the accuracy of determination cannot be kept high. Also, the conventional methods for quantitatively analyzing bone calcium, wherein the accuracy of determination can be kept high, have the problems in that large-scaled apparatuses must be used to carry out the methods and a long time is required for the determination to be carried out.

Accordingly, in U.S. patent application Ser. No. 691,900, the applicant proposed a novel method for quantitatively analyzing bone calcium, wherein energy subtraction processing is employed. Specifically, the applicant proposed a method for quantitatively analyzing bone calcium by carrying out energy subtraction processing wherein each of at least two recording media (such as stimulable phosphor sheets or sheets of X-ray film) is exposed to one of at least two kinds of radiation, which have different energy distributions and have passed through an object constituted of bones and soft tissues, radiation images of the object are thereby recorded on the recording media, each of the recording media is thereafter exposed to reading light, each said radiation image is photoelectrically detected and converted into a digital image signal made up of a series of image signal components representing each said radiation image, the image signal components of the digital image signals thus obtained, which image signal components represent corresponding picture elements in the radiation images, are then subtracted from each other, and a difference signal is thereby obtained which represents the image of only the bones represented by the radiation images. The proposed method for quantitatively analyzing bone calcium comprises the steps of:

i) recording a pattern of a bone calcium reference material, which simulates amounts of bone calcium varying step-wise, together with the pattern of said object when each of said radiation images of said object is recorded on each of said recording media, and ii) quantitatively analyzing bone calcium in the bones by comparing the image density of the patterns of the bones with the image density of the pattern of the bone calcium reference material, both patterns appearing in the image of only the bones (i.e., the bone image).

With the method for quantitatively analyzing bone calcium, wherein energy subtraction processing is employed, amounts of calcium in bones can be determined more easily and more accurately than with other conventional methods. However, when radiation is irradiated to an object and a radiation image of the object is thereby recorded on a recording medium, the radiation is scattered by tissues of the object. For such reasons, or the like, even if the amounts of bone calcium contained in different parts of bones are identical with each other, the image density of the patterns of these parts of the bones will vary slightly for different positions of the patterns of these parts of the bones in the radiation image. Therefore, the method for quantitatively analyzing bone calcium, wherein energy subtraction processing is employed, has the problem in that an error in finding the amount of bone calcium in a specific part of the bones is caused to occur by a difference in the position between the pattern of the specific part of the bones and the pattern of the bone calcium reference material in the radiation image.

SUMMARY OF THE INVENTION

The primary object of the present invention is to provide a method for quantitatively analyzing bone calcium, wherein energy subtraction processing is employed, and the accuracy with which the amount of bone calcium is determined is kept high by eliminating errors due to adverse effects of radiation scattered by tissues of an object, or the like.

The present invention provides a method for quantitatively analyzing bone calcium, which comprises the steps of:

i) exposing each of a plurality of recording media to one of several kinds of radiation, which have different energy distributions and have passed through an object and a bone calcium reference material, which is composed of a plurality of sections simulating amounts of bone calcium varying step-wise, the object being constituted of bones and soft tissues, whereby a plurality of radiation images are recorded on the recording media, ii) forming a bone image, in which only the patterns of the bones of the object have been formed or emphasized, from the plurality of the radiation images, iii) detecting background signal components, which represent a background region other than said patterns of the bones and a pattern of said bone calcium reference material in said bone image, from an image signal made up of a series of image signal components representing said bone image, iv) calculating the value of a difference between a mean value of the values of image signal components, which represent part of the pattern of each said section of said bone calcium reference material in said bone image, and a mean value of the values of background signal components, which represent areas in the vicinity of said pattern of each said section of said bone calcium reference material in said bone image, v) calculating the value of a difference between a mean value of the values of image signal components, which represent a pattern of a specific part of the bones in said bone image, and a mean value of the values of background signal components, which represent areas in the vicinity of said pattern of said specific part of the bones in said bone image, and vi) determining the amount of bone calcium in said specific part of the bones by comparing the value of the difference, which has been calculated for said pattern of said specific part of the bones in said bone image, with the values of the differences, which have been calculated for the patterns of the plurality of said sections of said bone calcium reference material in said bone image.

With the method for quantitatively analyzing bone calcium in accordance with the present invention, a calculation is made to find the value of the difference between the mean value of the values of image signal components, which represent part of the pattern of each section of the bone calcium reference material in the bone image, and the mean value of the values of background signal components, which represent areas in the vicinity of the pattern of each section of the bone calcium reference material in the bone image. Also, a calculation is made to find the value of the difference between the mean value of the values of image signal components, which represent the pattern of the specific part of the bones in the bone image, and the mean value of the values of background signal components, which represent areas in the vicinity of the pattern of the specific part of the bones in the bone image. Thereafter, the amount of bone calcium in the specific part of the bones is determined by comparing the value of the difference, which has been calculated for the pattern of the specific part of the bones in the bone image, with the values of the differences, which have been calculated for the patterns of the plurality of the sections of the bone calcium reference material in the bone image. Therefore, with the method for quantitatively analyzing bone calcium in accordance with the present invention, adverse effects from the background signal components including the components due to scattered radiation, or the like, can be eliminated, and the amount of bone calcium in the specific part of the bones can be determined accurately.

BRIEF DESCRIPTION OF THE DRAWINGS

FIG. 4 is an explanatory view showing how energy subtraction processing is carried out in the embodiment of the method for quantitatively analyzing bone calcium in accordance with the present invention, FIG. 5A is an explanatory view showing an example of how a calculation is made to find the value of a difference between a mean value of the values of image signal components, which represent part of a pattern of each section of a bone calcium reference material in a bone image, and a mean value of the values of background signal components, which represent areas in the vicinity of the pattern of each section of the bone calcium reference material in the bone image, FIG. 5B is an explanatory view showing an example of how a calculation is made to find the value of a difference between a mean value of the values of image signal components, which represent a pattern of a specific part of bones in a bone image, and a mean value of the values of background signal components, which represent areas in the vicinity of the pattern of the specific part of the bones in the bone image, FIG. 6 is a graph showing a straight line indicating the relationship between the amount of bone calcium and the difference value, which has been calculated for a pattern of a bone calcium reference material.

DESCRIPTION OF THE PREFERRED EMBODIMENTS

The present invention will hereinbelow be described in further detail with reference to the accompanying drawings.

An embodiment of the method for quantitatively analyzing bone calcium in accordance with the present invention will be described hereinbelow. In this embodiment, stimulable phosphor sheets are employed as recording media.

Figure 1A:
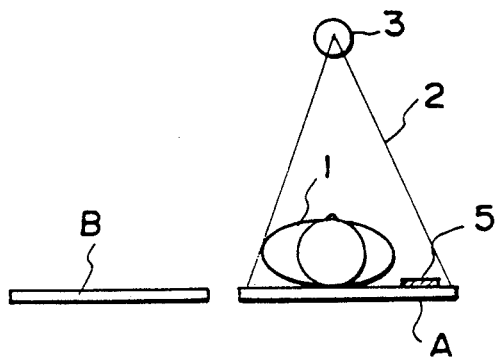
FIGS. 1A and 1B are side views showing examples of image recording steps in an embodiment of the method for quantitatively analyzing bone calcium in accordance with the present invention.

With reference to FIG. 1A, stimulable phosphor sheets A and B are sequentially exposed to X-rays 2, which have passed through an object 1 constituted of bones and soft tissues and which have different energy levels. Specifically, first, an X-ray image of the object 1 is stored on the stimulable phosphor sheet A. Thereafter, the stimulable phosphor sheet A is quickly removed from the position for exposure to the X-rays 2, and the stimulable phosphor sheet B is quickly set at the position for exposure to the X-rays 2. At the same time, the tube voltage of the X-ray source 3 is changed so that it produces the X-rays 2 having a different energy level. In this manner, an X-ray image of the object 1 is stored on the stimulable phosphor sheet B with the X-rays 2 having the different energy level. The positions of the stimulable phosphor sheets A and B with respect to the position of the object 1 are kept the same.

Figure 2:
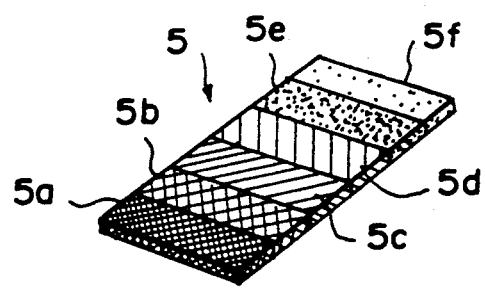
FIG. 2 is a perspective view showing an example of a bone calcium reference material which is used in an image recording step.

At this time, a bone calcium reference material (a phantom) 5, which is constituted of a plurality of sections the radiation absorption amounts of which are known and vary step-wise, is placed on each of the stimulable phosphor sheets A and B. In this manner, a pattern of the phantom 5 and the pattern of the object 1 are stored together on each of the stimulable phosphor sheets A and B. As shown in FIG. 2, the phantom 5 is constituted of sections 5a, 5b, 5c, 5d, 5e, and 5f, in which the content (wt %) of bone calcium, i.e. $CaCO_3$, varies step-wise. The contents of $CaCO_3$ in the sections 5a, 5b, 5c, 5d, 5e, and 5f are already known.

Figure 1B:
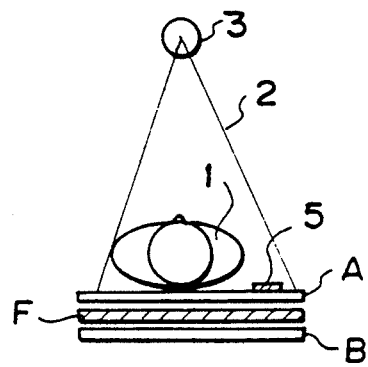

Alternatively, an image recording operation may be carried out in the manner shown in FIG. 1B. With reference to FIG. 1B, stimulable phosphor sheets A and B are placed one upon the other, and a filter F capable of absorbing part of radiation energy is inserted between the stimulable phosphor sheets A and B. The stimulable phosphor sheets A and B are exposed to X-rays 2, which have passed through an object 1 and a phantom 5. In this manner, the stimulable phosphor sheets A and B are simultaneously exposed to the X-rays 2 having different energy levels. The image recording operation is thus carried out for one-shot energy subtraction processing. One of techniques for carrying out one-shot energy subtraction processing is disclosed in, for example, U.S. Pat. No. 4,855,598.

Figure 3:
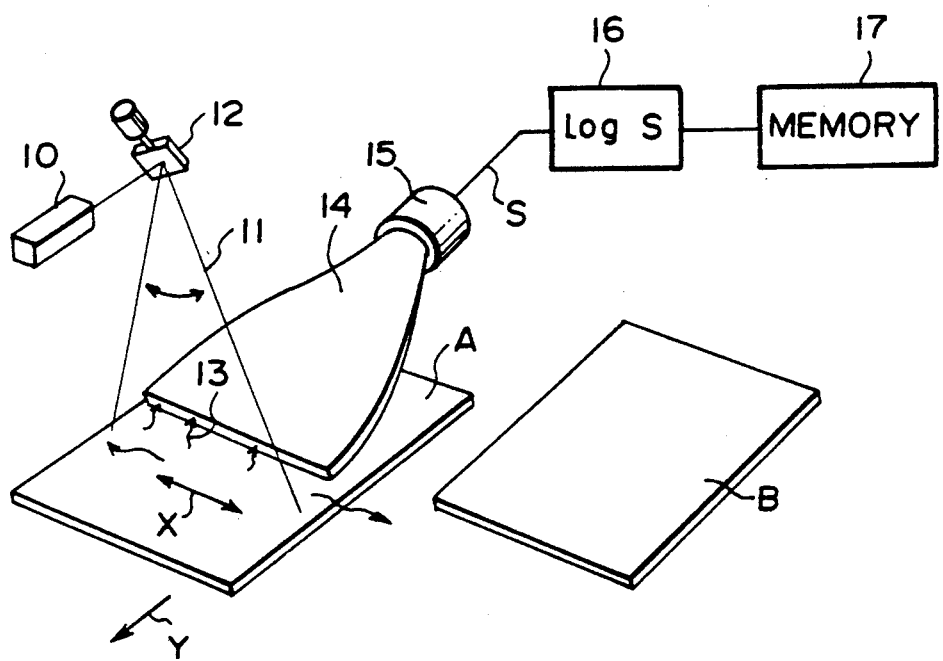
FIG. 3 is a perspective view showing an example of an image read-out step in the embodiment of the method for quantitatively analyzing bone calcium in accordance with the present invention.

In the manner described above with reference to FIG. 1A or FIG. 1B, two X-ray images are stored on the stimulable phosphor sheets A and B. Thereafter, in an image read-out means shown in FIG. 3, the X-ray images are read out from the stimulable phosphor sheets A and B, and digital image signals representing the X-ray images are thereby obtained. Specifically, first, the stimulable phosphor sheet A is moved in the sub-scanning direction indicated by the arrow Y. At the same time, a laser beam 11, which serves as stimulating rays, is produced by a laser beam source 10. The laser beam 11 is deflected by a scanning mirror 12 and caused to scan the stimulable phosphor sheet A in the main scanning directions indicated by the double-headed arrow X. When the stimulable phosphor sheet A is exposed to the laser beam 11, it emits light 13 in proportion to the amount of energy stored thereon during its exposure to the X-rays 2. The emitted light 13 enters a light guide member 14, which is made from a transparent acrylic plate, from its one edge face. The emitted light 13 is guided through repeated total reflection inside of the light guide member 14 and detected by a photomultiplier 15. The photomultiplier 15 generates an image signal S corresponding to the amount of the emitted light 13, i.e. representing the X-ray image stored on the stimulable phosphor sheet A.

The image signal S is converted into a digital image signal logSA having logarithmic values (logS) by a logarithmic converter 16 provided with an amplifier and an A/D converter. The digital image signal logSA is stored on a storage medium 17, such as a magnetic disk. Thereafter, the X-ray image stored on the stimulable phosphor sheet B is read out in the same manner as that described above. The digital image signal logSB representing the X-ray image stored on the stimulable phosphor sheet B is stored on the storage medium 17.

FIG. 4 shows how a subtraction process is carried out on the digital image signals logSA and logSB, which have been obtained in the manner described above. An image 18 is represented by the digital image signal logSA and was stored with the X-rays 2 produced at a low tube voltage (e.g. 60 kV) of the X-ray source 3. An image 19 was stored with the X-rays 2 produced at a high tube voltage (120 kV) of the X-ray source 3. The image 18 is composed of patterns 18$a$, 18$a$, . . . of the bones of the lumbar of a human body, a pattern 18$b$ of the soft tissues, and a pattern 18$c$ of the bone calcium reference material. Also, the image 19 is composed of patterns 19$a$, 19$a$, . . . of the bones of the lumbar of a human body, a pattern 19$b$ of the soft tissues, and a pattern 19$c$ of the bone calcium reference material.

The thickness, or the like, of the soft tissues varies markedly for different persons, and the corresponding patterns adversely affect the quantitative determination of the amount of bone calcium. Therefore, the image signal components of the digital image signals logSA and logSB are subtracted from each other which represent corresponding picture elements in the X-ray images 18 and 19. From the subtraction process, a bone image signal is obtained, which is expressed as $$\log S = A \log SA - B \log SB + C \quad (1)$$

wherein A, B and C denote coefficients. The bone image signal represents a bone image 20, in which the patterns 18$b$, 19$b$ of the soft tissues have been erased.

FIG. 5A is an explanatory view showing an example of how a calculation is made to find the value of a difference between a mean value SC of the values of image signal components, which represent a part C of a pattern 20$c$ of a section 5$a$ of the bone calcium reference material in the bone image 20, and a mean value SD of the values of background signal components, which represent areas D, D in the vicinity of the pattern 20$c$ of the section 5$a$ of the bone calcium reference material in the bone image 20. FIG. 5B is an explanatory view showing an example of how a calculation is made to find the value of a difference between a mean value SC' of the values of image signal components, which represent a pattern 20$a$ of a specific part C' of bones in the bone image 20, and a mean value SD' of the values of background signal components, which represent areas D', D' in the vicinity of the pattern 20$a$ of the specific part C' of the bones in the bone image 20.

First, as illustrated in FIG. 5A, a calculation is made to find the mean value SC of the values of image signal components, which represent the part C of the pattern 20$c$ of the section 5$a$ of the bone calcium reference material in the bone image 20. Also, a calculation is made to find the mean value SD of the values of background signal components, which represent the areas D, D in the vicinity of the pattern 20$c$ of the section 5$a$ of the bone calcium reference material in the bone image 20. Thereafter, the value of the difference, SC−SD, between the mean value SC of the values of the image signal components and the mean value SD of the values of the background signal components is calculated. By carrying out the calculation of the value of the difference, SC−SD, the background signal components, which represent the areas D, D in the vicinity of the pattern 20$c$ of the section 5$a$ of the bone calcium reference material in the bone image 20 and which take the mean value SD, are eliminated from the background signal components, which have been superposed upon the image signal components representing the part C of the pattern 20$c$ of the section 5$a$ of the bone calcium reference material. The values of the background signal components, which represent the areas D, D in the vicinity of the pattern 20$c$ of the section 5$a$ of the bone calcium reference material, are approximately equal to the values of the background signal components, which have been superposed upon the image signal components representing the part C of the pattern 20$c$ of the section 5$a$ of the bone calcium reference material. Therefore, the value of the difference, SC−SD, accurately represents the value of an image signal, which is free of the background signal components affected by the scattered radiation.

In the manner described above, calculations are made to find the values of the differences between the mean values of the values of image signal components, which represent parts of the patterns 20$c$, 20$c$, . . . of the sections 5$a$, 5$b$, 5$c$, 5$d$, 5$e$, and 5$f$ of the bone calcium reference material in the bone image 20, and the mean values of the values of background signal components, which represent the areas in the vicinity of the patterns 20$c$, 20$c$, . . . of the sections 5$a$, 5$b$, 5$c$, 5$d$, 5$e$, and 5$f$ of the bone calcium reference material in the bone image 20.

Also, in the same manner as that described above, a calculation is made to find the value of the difference, SC'−SD', between the mean value SC' of the values of image signal components, which represent the pattern 20$a$ of the specific part C' of bones in the bone image 20, and the mean value SD' of the values of the background signal components, which represent the areas D', D' in the vicinity of the pattern 20$a$ of the specific part C' of the bones in the bone image 20.

FIG. 6 is a graph showing a straight line 24 indicating the relationship between the amount of bone calcium and the difference value, which has been calculated in the manner described above for the pattern 20$c$ of the bone calcium reference material.

By way of example, when the value of the difference between the mean value of the values of image signal components, which represent the pattern 20$a$ of the specific part C' of bones in the bone image 20, and the mean value of the values of the background signal components, which represent the areas in the vicinity of the pattern 20$a$ of the specific part C' of the bones in the bone image 20, is equal to $\Delta S1$, the amount of bone calcium in the specific part C' of the bones is found as being V1.

In the aforesaid embodiment, the stimulable phosphor sheets are used. However, the method for quantitatively analyzing bone calcium in accordance with the present invention is also applicable when other recording media, such as X-ray film, are used.

Figure 7:
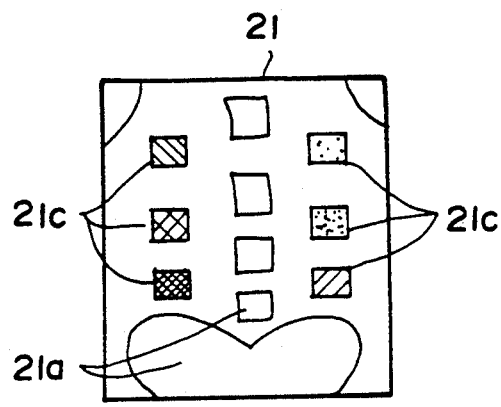
FIG. 7 is an explanatory view showing a different example of how a plurality of sections constituting a bone calcium reference material are located in an embodiment of the method for quantitatively analyzing bone calcium in accordance with the present invention.

Also, in the aforesaid embodiment, the bone calcium reference material (i.e., the phantom) 5 constituted of a plurality of sections, the radiation absorption amounts of which vary step-wise and which are combined with one another, is employed. Alternatively, as illustrated in FIG. 7, a plurality of sections of the bone calcium reference material, the radiation absorption amounts of which sections vary step-wise, may be spaced apart from one another. In FIG. 7, reference numeral 21 represents a bone image, and reference numerals 21c, 21c, ... represent the patterns of the sections of the bone calcium reference material.

Figure 8A:
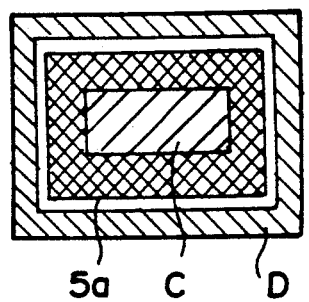
FIG. 8A is an explanatory view showing a different example of how a calculation is made to find the value of a difference between a mean value of the values of image signal components, which represent part of a pattern of each section of a bone calcium reference material in a bone image, and a mean value of the values of background signal components, which represent areas in the vicinity of the pattern of each section of the bone calcium reference material in the bone image.
Figure 8B:
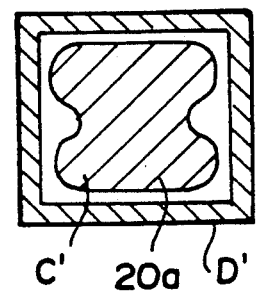
FIG. 8B is an explanatory view showing a different example of how a calculation is made to find the value of a difference between a mean value of the values of image signal components, which represent a pattern of a specific part of bones in a bone image, and a mean value of the values of background signal components, which represent areas in the vicinity of the pattern of the specific part of the bones in the bone image.

In the embodiment described above, the mean value SD of the values of the background signal components, which represent areas in the vicinity of the pattern 20c of each section of the bone calcium reference material in the bone image 20, is calculated from the values of the background signal components, which represent part of the areas in the vicinity of the pattern 20c of each section of the bone calcium reference material. Also, the mean value SD' of the values of the background signal components, which represent areas in the vicinity of the pattern 20a of the specific part C' of the bones in the bone image 20, is calculated from the values of the background signal components, which represent part of the areas in the vicinity of the pattern 20a of the specific part C' of the bones. However, in the method for quantitatively analyzing bone calcium in accordance with the present invention, the mean value SD of the values of the background signal components may be calculated from the values of the background signal components, which represent any of the areas in the vicinity of the pattern 20c of each section of the bone calcium reference material. Also, the mean value SD' of the values of the background signal components may be calculated from the values of the background signal components, which represent any of the areas in the vicinity of the pattern 20a of the specific part C' of the bones. For example, as illustrated in FIG. 8A, the mean value SD of the values of the background signal components may be calculated from the values of the background signal components, which represent the areas D surrounding the pattern 20c of the section 5a of the bone calcium reference material. Also, as illustrated in FIG. 8B, the mean value SD' of the values of the background signal components may be calculated from the values of the background signal components, which represent the areas D' surrounding the pattern 20a of the specific part C' of the bones.

Additionally, the calibration line 24 employed in the embodiment described above is approximated by the straight line. Alternatively, the calibration line may be a curve.

What is claimed is:

1. A method for quantitatively analyzing bone calcium, which comprises the steps of:

i) each of a plurality of recording media to one of several kinds of radiation, which have different energy distributions and have passed through an object and a bone calcium reference material, which is composed of a plurality of sections simulating amounts of bone calcium varying step-wise, the object being constituted of bones and soft tissues, whereby a plurality of radiation images are recorded on the recording media, ii) forming a bone image, in which only the patterns of the bones of the object have been formed or emphasized, from the plurality of the radiation images, iii) detecting background signal components, which represent a background region other than said patterns of the bones and a pattern of said bone calcium reference material in said bone image, from an image signal made up of a series of image signal components representing said bone image, iv) calculating the value of a difference between a mean value of the values of image signal components, which represent part of the pattern of each said section of said bone calcium reference material in said bone image, and a mean value of the values of background signal components, which represent areas in the vicinity of said pattern of each said section of said bone calcium reference material in said bone image, v) calculating the value of a difference between a mean value of the values of image signal components, which represent a pattern of a specific part of the bones in said bone image, and a mean value of the values of background signal components, which represent areas in the vicinity of said pattern of said specific part of the bones in said bone image, and vi) determining the amount of bone calcium in said specific part of the bones by comparing the value of the difference, which has been calculated for said pattern of said specific part of the bones in said bone image, with the values of the differences, which have been calculated for the patterns of the plurality of said sections of said bone calcium reference material in said bone image.

2. A method as defined in claim 1 wherein said recording media are stimulable phosphor sheets.

3. A method as defined in claim 1 wherein said recording media are photographic film.

4. A method as defined in claim 1 wherein said radiation images are X-ray images.

* * * * *